US010620335B2

(12) United States Patent
Ashe et al.

(10) Patent No.: US 10,620,335 B2
(45) Date of Patent: Apr. 14, 2020

(54) ROTATING FREQUENCIES OF TRANSMITTERS

(71) Applicant: Ascension Technology Corporation, Shelburne, VT (US)

(72) Inventors: Westley S. Ashe, Hinesburg, VT (US); Vladimir F. Kogan, Shelburne, VT (US)

(73) Assignee: Ascension Technology Corporation, Shelburne, VT (US)

( * ) Notice: Subject to any disclaimer, the term of this patent is extended or adjusted under 35 U.S.C. 154(b) by 77 days.

(21) Appl. No.: 15/957,403

(22) Filed: Apr. 19, 2018

(65) Prior Publication Data

US 2018/0321417 A1    Nov. 8, 2018

Related U.S. Application Data

(60) Provisional application No. 62/500,118, filed on May 2, 2017.

(51) Int. Cl.
| | |
|---|---|
| *G01V 3/38* | (2006.01) |
| *G01V 3/10* | (2006.01) |
| *A61B 34/20* | (2016.01) |
| *A61B 5/06* | (2006.01) |
| *A61B 5/00* | (2006.01) |

(52) U.S. Cl.
CPC ................. *G01V 3/38* (2013.01); *A61B 5/062* (2013.01); *A61B 34/20* (2016.02); *G01V 3/10* (2013.01); *G01V 3/101* (2013.01); *A61B 5/743* (2013.01); *A61B 2034/2051* (2016.02)

(58) Field of Classification Search
CPC . G01V 3/38; G01V 3/101; A61B 5/62; A61B 5/743
See application file for complete search history.

(56) References Cited

U.S. PATENT DOCUMENTS

| | | |
|---|---|---|
| 2,753,469 A | 7/1956 | Statham et al. |
| 3,306,113 A | 2/1967 | Tuccinardi |
| 3,516,294 A | 6/1970 | Schmieder |
| 3,868,565 A | 2/1975 | Kuipers |
| 3,983,474 A | 9/1976 | Kuipers |
| 4,023,278 A | 5/1977 | Hoyt |
| 4,047,439 A | 9/1977 | Russell et al. |
| 4,054,881 A | 10/1977 | Raab |
| 4,287,809 A | 9/1981 | Egli et al. |
| 4,557,667 A | 12/1985 | Delassus et al. |
| 4,718,276 A | 1/1988 | Laughlin |
| 4,808,079 A | 2/1989 | Crowley et al. |
| 4,818,185 A | 4/1989 | Alexeff |
| 4,905,517 A | 3/1990 | Crowe et al. |
| 4,922,753 A | 5/1990 | Idogaki et al. |

(Continued)

*Primary Examiner* — Dominic E Hawkins (74) *Attorney, Agent, or Firm* — Fish & Richardson P.C.

(57) ABSTRACT

A system comprising: a transmitter that includes at least three coils, the transmitter configured to generate magnetic fields; a sensor that includes at least three coils, the sensor configured to provide sensor signals that correspond to the magnetic fields generated by the transmitter; and a computing device in communication with the transmitter and the sensor, the computing device configured to compare a first sensor signal and a second sensor signal, and based on the comparison, determine whether any of the sensor coils are locked to a corresponding frequency out-of-phase.

25 Claims, 4 Drawing Sheets

(56) References Cited

U.S. PATENT DOCUMENTS

| | | |
|---|---|---|
| 4,984,463 A | 1/1991 | Idogaki et al. |
| 4,991,438 A | 2/1991 | Evans |
| 5,007,292 A | 4/1991 | Crowe et al. |
| 5,461,919 A | 10/1995 | Laughlin |
| 5,665,912 A | 9/1997 | Laughlin |
| 5,780,741 A | 7/1998 | Raj |
| 5,908,987 A | 6/1999 | Raj |
| 6,020,891 A | 2/2000 | Rekimoto |
| 6,173,611 B1 | 1/2001 | Laughlin |
| 6,374,673 B1 | 4/2002 | Schendel |
| 6,380,732 B1 | 4/2002 | Gilboa |
| 6,404,340 B1 | 6/2002 | Paradiso et al. |
| 6,754,609 B2 | 6/2004 | Lescourret |
| 6,789,043 B1 | 9/2004 | Nelson et al. |
| 6,891,527 B1 | 5/2005 | Chapman et al. |
| 7,015,859 B2 | 3/2006 | Anderson |
| 7,074,175 B2 | 7/2006 | Handy et al. |
| 7,149,691 B2 | 12/2006 | Balan et al. |
| 7,175,912 B2 | 2/2007 | Chen et al. |
| 7,178,399 B2 | 2/2007 | Simonenko et al. |
| 7,204,581 B2 | 4/2007 | Peeters |
| 7,296,469 B2 | 11/2007 | Simonenko et al. |
| 7,580,676 B2 | 8/2009 | Anderson |
| 7,700,193 B2 | 4/2010 | Chen et al. |
| 7,715,898 B2 | 5/2010 | Anderson |
| 7,819,795 B1 | 10/2010 | Seeney et al. |
| 7,969,143 B2 | 6/2011 | Gilboa |
| 8,354,837 B2 | 1/2013 | Anderson |
| 8,436,808 B2 | 5/2013 | Chapman et al. |
| 8,906,019 B2 | 12/2014 | Mueller |
| 8,944,067 B2 | 2/2015 | Robinson et al. |
| 9,017,713 B2 | 4/2015 | Tishin et al. |
| 9,186,317 B2 | 11/2015 | Smyth et al. |
| 9,196,405 B2 | 11/2015 | Schlenoff et al. |
| 2001/0038354 A1 | 11/2001 | Gilboa |
| 2002/0030483 A1 | 3/2002 | Gilboa |
| 2003/0139895 A1 | 7/2003 | Lescourret |
| 2005/0104776 A1 | 5/2005 | Anderson |
| 2005/0110773 A1 | 5/2005 | Chapman et al. |
| 2005/0119725 A1 | 6/2005 | Wang et al. |
| 2007/0078334 A1 | 4/2007 | Scully et al. |
| 2007/0264199 A1 | 11/2007 | Labhasetwar et al. |
| 2008/0183064 A1* | 7/2008 | Chandonnet ............. A61B 5/06 600/407 |
| 2013/0241894 A1 | 9/2013 | Chapman et al. |
| 2014/0276010 A1* | 9/2014 | Anderson ............. A61B 5/062 600/424 |
| 2015/0285612 A1* | 10/2015 | Miles ...................... G01V 3/12 702/150 |
| 2016/0011013 A1 | 1/2016 | Pedrotti et al. |
| 2016/0015292 A1* | 1/2016 | Lorraine ............. A61B 34/20 600/424 |
| 2016/0259404 A1 | 9/2016 | Woods |
| 2016/0294225 A1 | 10/2016 | Blum et al. |
| 2017/0242087 A1* | 8/2017 | Zho .................. G01R 33/5617 |
| 2018/0116549 A1* | 5/2018 | Morgan ................ A61B 5/062 |
| 2019/0046274 A1* | 2/2019 | Mikuszeit ............ G01D 5/2013 |

* cited by examiner

$$S_{ABC} = \begin{array}{c} x \\ y \\ z \end{array} \begin{array}{ccc} X & Y & Z \\ \left[ \begin{array}{ccc} S_{Xx} & S_{Yx} & S_{Zx} \\ S_{Xy} & S_{Yy} & S_{Zy} \\ S_{Xz} & S_{Yz} & S_{Zz} \end{array} \right] \end{array}$$

$$S_{BCA} = \begin{matrix} x \\ y \\ z \end{matrix} \begin{bmatrix} S_{Xx} & S_{Yx} & S_{Zx} \\ S_{Xy} & S_{Yy} & S_{Zy} \\ S_{Xz} & S_{Yz} & S_{Zz} \end{bmatrix} \begin{matrix} X & Y & Z \end{matrix}$$

$$S_{BCA} = \begin{matrix} x \\ y \\ z \end{matrix} \begin{bmatrix} S_{Xx} & -S_{Yx} & -S_{Zx} \\ S_{Xy} & -S_{Yy} & -S_{Zy} \\ S_{Xz} & -S_{Yz} & -S_{Zz} \end{bmatrix} \begin{matrix} X & Y & Z \end{matrix}$$

FIG. 3B

ROTATING FREQUENCIES OF TRANSMITTERS

CLAIM OF PRIORITY

This application claims priority under 35 USC § 119(e) to U.S. Patent Application Ser. No. 62/500,118, filed on May 2, 2017, the entire contents of which are hereby incorporated by reference.

TECHNICAL FIELD

This disclosure relates to rotating frequencies of transmitters.

BACKGROUND

Electromagnetic Tracking (EMT) systems are used to aid in locating instruments and anatomy in medical procedures. These systems utilize a magnetic transmitter in proximity to a magnetic sensor. The sensor can be spatially located relative to the transmitter.

SUMMARY

An Electromagnetic Tracking (EMT) system can be used to track the position and/or orientation of a sensor relative to a transmitter. A demodulation algorithm may be used to measure characteristics of an EM field generated by the transmitter. Such a demodulation algorithm requires locking the demodulating signal to a measured sensor signal. Once the locking occurs, components of the sensor signal will have signs (e.g., positive or negative) that correspond to the orientation of the sensor. For example, when the sensor reverses orientation in a particular axis, the components of the sensor signal corresponding to the particular axis will change sign. However, if the demodulating signal is locked to the sensor signal at a time in which the orientation of the sensor in the particular axis is reversed, then the components of the sensor signal for the particular axis will have the opposite sign. In other words, the true orientation of the sensor in the particular axis may be positive according to a right-hand-rule, but the sensor signal may indicate that the orientation of the sensor is negative.

The systems and techniques described herein provide a way to ascertain the orientation of the sensor without first maintaining the sensor in a known orientation at the time of locking. Coils of the transmitter may be configured to initially run at three different frequencies A, B, and C. A first sensor signal is obtained by the sensor. The frequencies may then be rotated such that the coils run at different frequencies B, C, and A. A second sensor signal is obtained by the sensor. The two sensor signals can be compared. Depending on which components of the sensor signal change sign after the frequency rotation, it can be determined which (if any) frequencies were locked to the sensor signal out-of-phase, and if necessary, appropriate correction can be provided (e.g., by mathematically adjusting the sensor signal).

In one aspect, a system includes a transmitter that includes at least three coils. The transmitter is configured to generate magnetic fields. The system also includes a sensor that includes at least three coils. The sensor is configured to provide sensor signals that correspond to the magnetic fields generated by the transmitter. The system also includes a computing device in communication with the transmitter and the sensor. The computing device is configured to cause the transmitter to generate a first magnetic field in which a first transmitter coil provides a portion of the first magnetic field at a first frequency, a second transmitter coil provides a portion of the first magnetic field at a second frequency, and a third transmitter coil provides a portion of the first magnetic field at a third frequency. The computing device is also configured to receive, from the sensor, a first sensor signal that corresponds to the first magnetic field. The first sensor signal includes, for each sensor coil, a measurement component that corresponds to each transmitter coil. The first sensor signal is locked to a demodulating signal such that a first sensor coil, a second sensor coil, and a third sensor coil are each locked to the first frequency, the second frequency, and the third frequency. The computing device is also configured to cause the transmitter to generate a second magnetic field in which the first transmitter coil provides a portion of the second magnetic field at the second frequency, the second transmitter coil provides a portion of the second magnetic field at the third frequency, and the third transmitter coil provides a portion of the second magnetic field at the first frequency. The computing device is also configured to receive, from the sensor, a second sensor signal that corresponds to the second magnetic field. The second sensor signal includes, for each sensor coil, a measurement component that corresponds to each transmitter coil. The computing device is also configured to compare the first sensor signal and the second sensor signal. The computing device is also configured to, based on the comparison, determine whether any of the sensor coils are locked to its corresponding frequency out-of-phase.

Implementations can include one or more of the following features.

In some implementations, comparing the first sensor signal and the second sensor signal includes comparing the signs of the measurement components that correspond to the first transmitter coil in the first sensor signal to the signs of the measurements components that correspond to the first transmitter coil in the second sensor signal. Comparing the first sensor signal and the second sensor signal also includes comparing the signs of the measurement components that correspond to the second transmitter coil in the first sensor signal to the signs of the measurements components that correspond to the second transmitter coil in the second sensor signal. Comparing the first sensor signal and the second sensor signal also includes comparing the signs of the measurement components that correspond to the third transmitter coil in the first sensor signal to the signs of the measurements components that correspond to the third transmitter coil in the second sensor signal.

In some implementations, if the signs of the measurement components that correspond to the first transmitter coil in the first sensor signal are the same as the signs of the measurements components that correspond to the first transmitter coil in the second sensor signal (e.g., the signs of the measurement components for the first transmitter coil did not change), a determination is made that the first frequency and the second frequency are locked out-of-phase. If the signs of the measurement components that correspond to the second transmitter coil in the first sensor signal are the same as the signs of the measurements components that correspond to the second transmitter coil in the second sensor signal (e.g., the signs of the measurement components for the second transmitter coil did not change), a determination is made that the second frequency and the third frequency are locked out-of-phase. If the signs of the measurement components that correspond to the third transmitter coil in the first sensor signal are the same as the signs of the measurements components that correspond to the third transmitter coil in the second sensor signal (e.g., the signs of the measurement components for the third transmitter coil did not change), a determination is made that the third frequency and the first frequency are locked out-of-phase.

In some implementations, the computing device is further configured to mathematically correct sensor signals provided by the sensor based on the determination of whether any of the sensor coils are locked to its corresponding frequency out-of-phase.

In some implementations, mathematically correcting the sensor signals includes changing a sign of measurement components of the sensor signals.

In some implementations, the first sensor signal and the second sensor signal are locked to the demodulating signal by a phase-locked loop, and mathematically correcting the sensor signals provided by the sensor occurs outside of the phase-locked loop.

In some implementations, the computing device is further configured to change a phase of the demodulating signal to cause the frequencies that are determined to be locked out-of-phase to become locked in-phase.

In some implementations, the first sensor signal and the second sensor signal include voltages that are generated based on interaction between the sensor and the magnetic field generated by the transmitter.

In some implementations, values of the voltages are indicative of the orientation and position of the sensor relative to the transmitter.

In some implementations, the sensor is a three-axis sensor that includes a concentric, collocated set of sensor coils.

In some implementations, the transmitter is a three-axis transmitter that includes a concentric, collocated set of transmitter coils.

In some implementations, the first sensor signal and the second sensor signal are locked to the demodulating signal by a phase-locked loop.

In some implementations, the system also includes a frequency synthesizer that is configured to continuously generate a first waveform of the first frequency, a second waveform of the second frequency, and a third waveform of the third frequency.

In some implementations, the first waveform is provided to the first transmitter coil during generation of the first magnetic field, the second waveform is provided to the second transmitter coil during generation of the first magnetic field, and the third waveform is provided to the third transmitter coil during generation of the first magnetic field.

In some implementations, the first waveform is provided to the third transmitter coil during generation of the second magnetic field, the second waveform is provided to the first transmitter coil during generation of the second magnetic field, and the third waveform is provided to the second transmitter coil during generation of the second magnetic field.

In some implementations, the first waveform is re-routed from the first transmitter coil to the third transmitter coil, the second waveform is re-rerouted from the second transmitter coil to the first transmitter coil, and the third waveform is re-routed from the third transmitter coil to the second transmitter coil, when the transmitter begins to generate the second magnetic field.

In some implementations, the first waveform, the second waveform, and the third waveform are each physically re-routed.

In some implementations, the first sensor signal and the second sensor signal are locked to the demodulating signal by a phase-locked loop, and demodulation phases of the phase-locked loop are continuous and stable throughout and after the re-routing of the waveforms.

In another aspect, a method includes causing a transmitter to generate a first magnetic field in which a first transmitter coil provides a portion of the first magnetic field at a first frequency, a second transmitter coil provides a portion of the first magnetic field at a second frequency, and a third transmitter coil provides a portion of the first magnetic field at a third frequency. The method also includes receiving, from a sensor, a first sensor signal that corresponds to the first magnetic field. The first sensor signal includes, for each of at least three sensor coils, a measurement component that corresponds to each transmitter coil. The first sensor signal is locked to a demodulating signal such that a first sensor coil, a second sensor coil, and a third sensor coil are each locked to the first frequency, the second frequency, and the third frequency. The method also includes causing the transmitter to generate a second magnetic field in which the first transmitter coil provides a portion of the second magnetic field at the second frequency, the second transmitter coil provides a portion of the second magnetic field at the third frequency, and the third transmitter coil provides a portion of the second magnetic field at the first frequency. The method also includes receiving, from the sensor, a second sensor signal that corresponds to the second magnetic field. The second sensor signal includes, for each sensor coil, a measurement component that corresponds to each transmitter coil. The method also includes comparing the first sensor signal and the second sensor signal. The method also includes, based on the comparison, determining whether any of the sensor coils are locked to its corresponding frequency out-of-phase.

In another aspect, a computer-readable medium includes instructions that when executed by a processor perform a method including causing a transmitter to generate a first magnetic field in which a first transmitter coil provides a portion of the first magnetic field at a first frequency, a second transmitter coil provides a portion of the first magnetic field at a second frequency, and a third transmitter coil provides a portion of the first magnetic field at a third frequency. The method also includes receiving, from a sensor, a first sensor signal that corresponds to the first magnetic field. The first sensor signal includes, for each of at least three sensor coils, a measurement component that corresponds to each transmitter coil. The first sensor signal is locked to a demodulating signal such that a first sensor coil, a second sensor coil, and a third sensor coil are each locked to the first frequency, the second frequency, and the third frequency. The method also includes causing the transmitter to generate a second magnetic field in which the first transmitter coil provides a portion of the second magnetic field at the second frequency, the second transmitter coil provides a portion of the second magnetic field at the third frequency, and the third transmitter coil provides a portion of the second magnetic field at the first frequency. The method also includes receiving, from the sensor, a second sensor signal that corresponds to the second magnetic field. The second sensor signal includes, for each sensor coil, a measurement component that corresponds to each transmitter coil. The method also includes comparing the first sensor signal and the second sensor signal. The method also includes, based on the comparison, determining whether any of the sensor coils are locked to its corresponding frequency out-of-phase.

In another aspect, a system includes a transmitter that includes at least three coils. The transmitter is configured to generate magnetic fields. The system also includes a sensor that includes at least three coils. The sensor is configured to provide sensor signals that correspond to the magnetic fields generated by the transmitter. The system also includes a computing device in communication with the transmitter and the sensor. The computing device is configured to cause the transmitter to generate a magnetic field according to a time-division-multiplexing technique in which a first transmitter coil provides a portion of the magnetic field at a particular frequency, a second transmitter coil provides a portion of the magnetic field at the particular frequency, and a third transmitter coil provides a portion of the magnetic field at the particular frequency. The transmitter coils are exited one at a time such that the respective portions of the magnetic field are provided one at a time. The computing device is also configured to receive, from the sensor, a sensor signal that corresponds to the magnetic field. The sensor signal includes, for each sensor coil, a measurement component that corresponds to each transmitter coil. The sensor signal is locked to a demodulating signal such that a first sensor coil, a second sensor coil, and a third sensor coil are each locked to the particular frequency. The computing device is also configured to determine whether the sensor signal is expressed in a geometric orientation convention that matches a geometric orientation convention of the transmitter. The computing device is also configured to determine that the demodulating signal is locked to the sensor signal out-of-phase if the geometric orientation convention of the sensor signal is determined to not match the geometric orientation convention of the transmitter.

Implementations can include one or more of the following features.

In some implementations, determining that the demodulating signal is locked to the sensor signal out-of-phase includes determining that the sensor coils are locked to the particular frequency out-of-phase.

In some implementations, the computing device is further configured to change a phase of the demodulating signal to cause the particular frequency to become locked in-phase.

In some implementations, the geometric orientation convention of the sensor signal and the geometric orientation convention of the transmitter are each either right-handed or left-handed.

In some implementations, the transmitter is right-handed if the transmitter has a coordinate system that follows the right-hand rule, and the transmitter is left-handed if the transmitter has a coordinate system that follows the left-hand rule.

The details of one or more embodiments of the subject matter described herein are set forth in the accompanying drawings and the description below. Other features, objects, and advantages of the subject matter will be apparent from the description and drawings, and from the claims.

DETAILED DESCRIPTION

An Electromagnetic Tracking (EMT) system can be used in surgical settings to track a piece of medical equipment, a robotic arm, etc., thereby allowing its respective three-dimensional location and orientation to be known to a medical professional (e.g., a surgeon) during a medical procedure. Such electromagnetic tracking can be used for guidance purposes in image-guided procedures, and in some cases may allow for reduced reliance on other imaging modalities, such as fluoroscopy, which can expose the patient to health risk of ionizing radiation.

In general, a transmitter having one or more coils is configured to generate an alternating current (AC) EM field. A sensor having one or more coils that is in proximity to the generated EM field is configured to measure characteristics of the generated EM field. The measurements are based on the position and orientation of the sensor relative to the transmitter. For example, when the sensor is located at a particular position and orientation, the EM field at that particular location may have particular characteristics. The sensor can measure the characteristics of the EM field and provide such measurements to a computing device in the form of a sensor signal. Using information related to the generated EM field and the sensor signal received from the sensor, the computing device can determine the position and/or orientation of the sensor (and, e.g., the position and/or orientation of a medical device in which the sensor is incorporated).

One or more demodulation algorithms may be used to measure the characteristics of the EM field. Such demodulation algorithms require aligning (e.g., locking) the demodulating signal to the sensor signal. When the generated EM field (e.g., and thus the sensor signal) and the demodulating signal are generated from separate reference signals, a phase-locked loop (PLL) may be used to lock the demodulating signal to the sensor signal. Once the demodulating signal is locked to the sensor signal, the sensor signal will have a sign that corresponds to the orientation of the sensor. For example, when the sensor is in a non-reversed orientation, the sensor signal may have a positive sign; when the sensor is in a reversed orientation, the sensor signal may have a negative sign.

Typically, before the start of a procedure, the sensor is maintained in a known orientation (e.g., a non-reversed orientation) and the demodulating signal is locked to the sensor signal. This procedure ensures that the sensor will provide a sensor signal having a positive sign when the sensor is in a non-reversed orientation; similarly, the sensor will provide a sensor signal having a negative sign when the sensor is in a reversed polarity. However, such an initialization procedure requires time and effort on the part of the technician/medical personnel. Further, if the sensor were to be unlocked from the demodulating signal (e.g., if the sensor loses connection), re-initialization is required. Such initialization is sometimes referred to as "spatial rotation".

The systems and techniques described herein provide a way to determine whether the frequencies of the demodulating signal were locked to the sensor signal in-phase or out-of-phase using a "frequency rotation" technique. The orientation of the sensor can be ascertained without first maintaining the sensor in a known orientation. A correlation can be determined between the signs of components of the sensor signal and the orientation of the sensor. If it is determined that any of the frequencies have been locked out-of-phase, the system can mathematically correct the sensor signal to compensate for the components of the sensor signal that have an incorrect sign.

Figure 1:
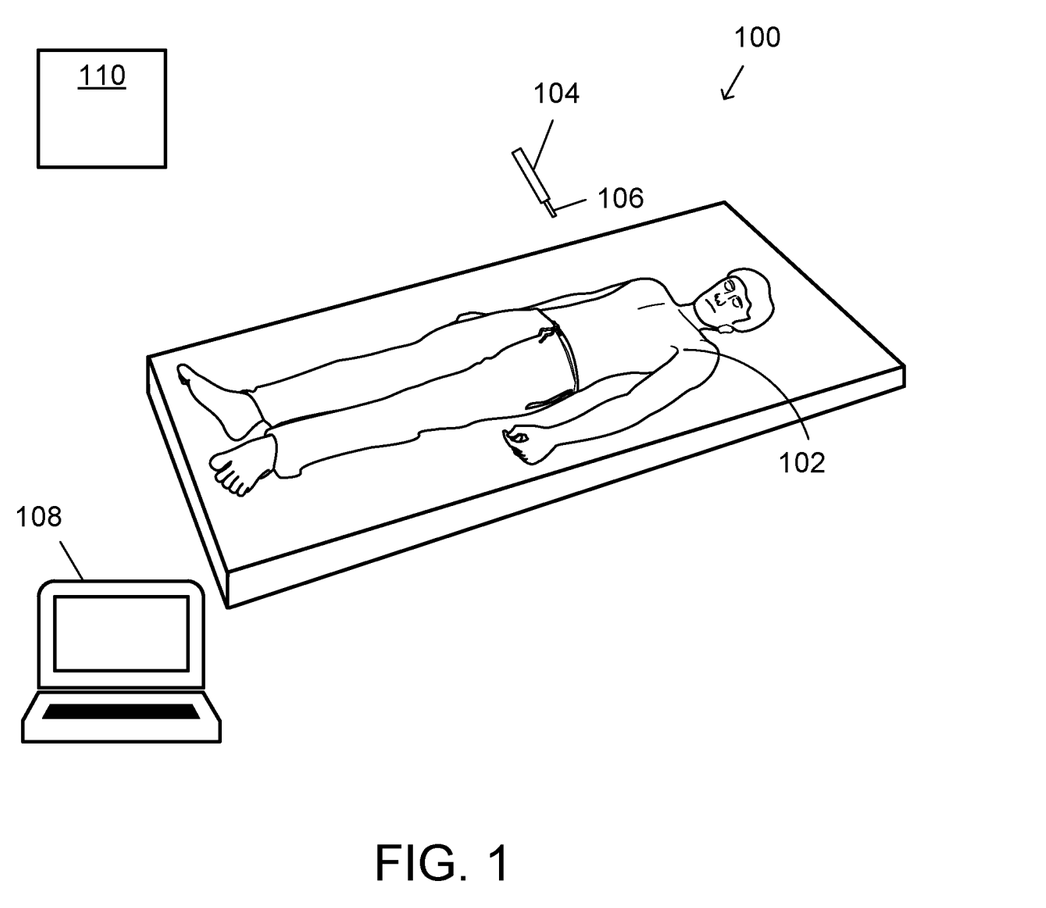
FIG. 1 is a schematic diagram of an Electromagnetic Tracking (EMT) system that includes a computer, a sensor, and a transmitter.

FIG. 1 presents an exemplary embodiment of the EMT system 100, which can be used for image-guided medical procedures performed on a patient 102. The system 100 may include a freely moving medical instrument 104, which can include any manner of surgical tools and devices for use in medical treatment. The system 100 permits targeting of an anatomical organ, structure, or vessel for visualization, diagnostic, interventional purposes, etc. Instruments for use in the EMT system 100 typically include one or more magnetic sensors including one or more coils. For example, the instrument 104 may include a three-axis magnetic sensor 106 that includes three sensors coils—an x-coil for making x-component measurements (e.g., in an x-axis), a y-coil for making y-component measurements (e.g., in a y-axis), and a z-coil for making z-component measurements (e.g., in a z-axis). In some implementations, the sensor coils are formed as a concentric, collocated set of sensor coils. The sensor 106 may be embedded in a channel or affixed to a tip of the instrument 104. The particular sensor 106 employed by the system 100 may be determined by the procedure type and/or the measurement performance requirements. In the illustrated example, the sensor 106 is connected to an electronic unit or a computing device, such as a computer 108, via a wireless connection.

Under control of circuitry for energizing magnetic fields, the sensor 106 measures its instantaneous position (x, y, z) and orientation angles (azimuth, altitude, roll) in three-dimensional space relative to a transmitter 110. Like the sensor 106, the particular transmitter employed by the system 100 may be determined by the procedure type, measurement performance requirements, etc. In the illustrated example, the transmitter 110 may be a three-axis magnetic transmitter that includes three transmitter coils— an X-coil for generating an X-component of an EM field, a Y-coil for generating a Y-component of the EM field, and a Z-coil for generating a Z-component of the EM field. That is, each transmitter coil is configured to provide a portion of the EM field. In some implementations, the transmitter coils are formed as a concentric, collocated set of transmitter coils The transmitter 110 is typically fixed in space beside, above, or beneath the patient or on medical equipment, where it acts as the reference frame for the measurements provided by the sensor 106. In some implementations, the transmitter 110 may be designed to minimize and/or negate the effect of distorters beneath its surface, such as procedural tables and/or equipment. The measurements provided by the sensor 106 and transmitter 110 provide sufficient information to navigate the instrument 104 outside or within the body of the patient 102 for diagnostic and interventional purposes, in some cases while providing visual feedback.

In some implementations, the computer 108 is an imaging computer that is configured to provide imaging capabilities to the system 100. The imaging computer 108, which in the illustrated example is in wireless communication with the sensor 106 and transmitter 110, is configured to store pre-acquired or intra-operative images of the patient 102 in an image database. Such images may then be input to imaging software for registration and visualization purposes. During the medical procedure, the three-dimensional location of the instrument 104 can be tracked relative to the anatomy of the patient 102 and the pre-acquired or inter-operative images and shown in real time on a display of the computer 108. When the instrument 104 is advance toward the target of interest within the body of the patient 102, the transmitter 110 can be activated and energized, thus producing measurable signals (e.g., voltage signals) in the sensor 106. These signals are processed and the three-dimensional location is computed for transmission to the computer 108. In some implementations, the computer 108 includes a guidance electronics unit that is configured to process the voltages in order to provide the three-dimensional location.

In some implementations, before the start of the procedure, one or more protocols are implemented. One protocol may initialize the instrument 104 and sensor 106 to prepare for tracking by the computer 108. Configuration data, such as instrument type, part number, sensor location in the instrument, calibration data, etc. may be stored in a memory of the computer 108. From this point forward, the system 100 may automatically provide the imaging software with specific configuration of the attached instrument 104. In such implementations, no manual entry of medical instrument data by the physician may be required. Another protocol may correlate the instrument 104, imaging modality, and patient reference frames so that the physician can guide the instrument intuitively within the patient 102 by following three-dimensional visualization cues. Once these protocols have been accomplished, the computer 108 can continuously receive instrument guidance data at the patient 102 and align the data with locations on the display of the computer 108. In this manner, as the physician moved the instrument 104 to a target within the body of the patient 102, the physician also sees an image on the display of an icon that corresponds to the instrument 104 relative to target images of the patient 102. The control of the guidance data and integration with scanned images may be a function of the three-dimensional software operable on the computer 108.

Figure 2:
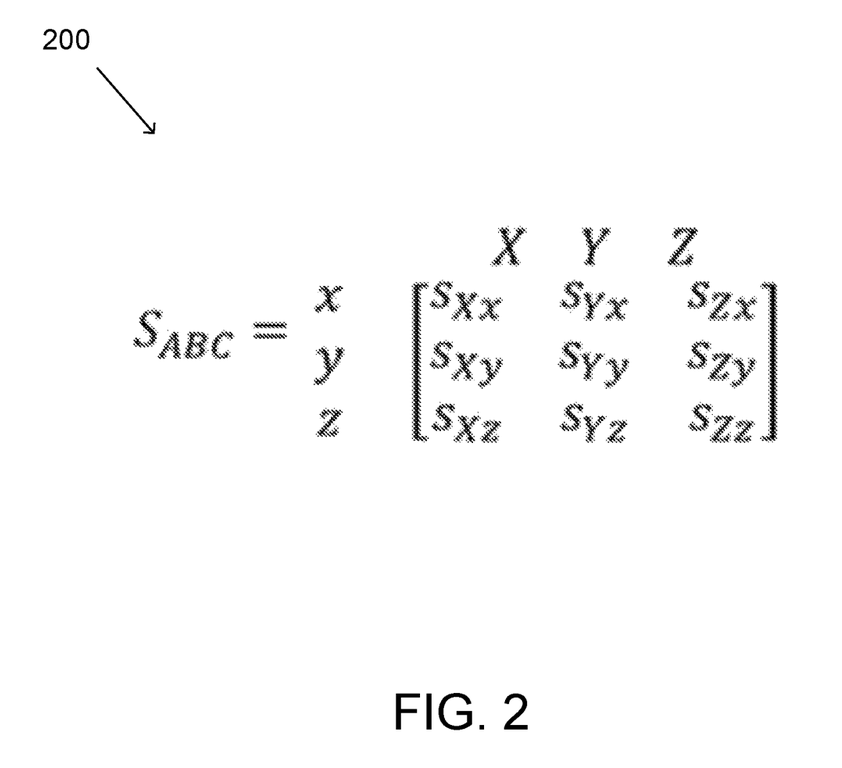
FIG. 2 shows an example of a sensor signal in a matrix representation.

In general, the EM field generated by the transmitter 110 has characteristics that can be measured by the sensor 106. For example, as the sensor 106 changes position in proximity to the transmitter 110, the x-, y-, and z-coils can each measure characteristics of the X-component, the Y-component, and the Z-component of the EM field, providing nine total components of the sensor signal. FIG. 2 shows an example of a sensor signal in a matrix representation 200. The matrix representation of the sensor signal is sometimes referred to as an S-matrix (e.g., a 3×3 matrix) in which the columns represent the X-, Y-, and Z-coils of the transmitter 110 and the rows represent the x-, y-, and z-coils of the sensor 106. In the illustrated example, the X-coil is running at frequency A, the Y-coil is running at frequency B, and the Z-coil is running at frequency C, which is denoted as sensor signal $S_{ABC}$.

The $s_{Xx}$ component of the S-matrix represents the measurement of the X-component of the generated EM field made by the x-coil of the sensor 106; the $s_{Xy}$ component of the S-matrix represents the measurement of the X-component of the generated EM field made by the y-coil of the sensor 106; etc.

Figure 1A:
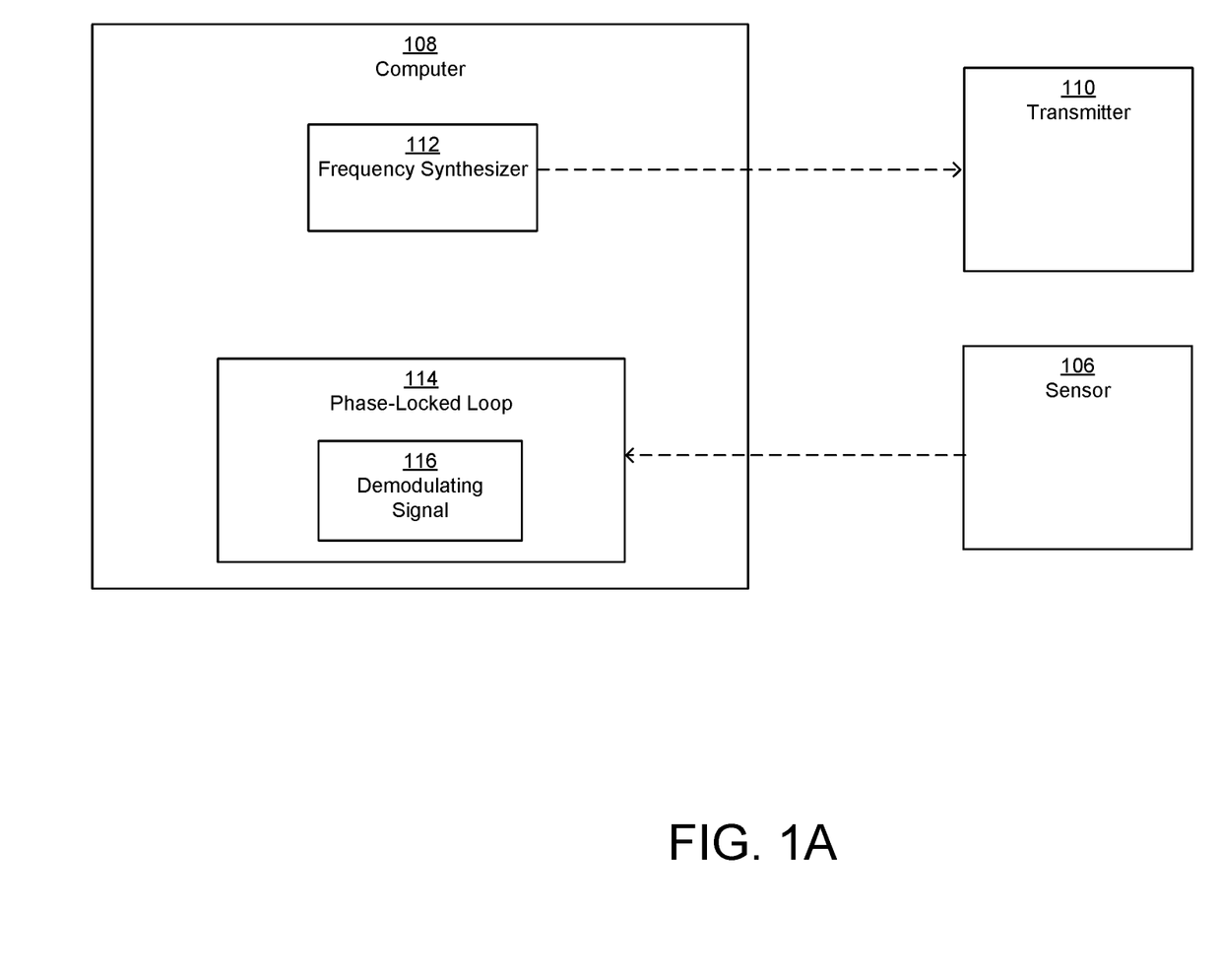
FIG. 1A shows an example of the computer, the sensor, and the transmitter of FIG. 1.

Referring to FIG. 1A, before the start of a procedure, a demodulation algorithm may be locked to the sensor signal. A phase-locked loop (PLL) 114 may be used to lock a demodulating signal 116 to the sensor signal. For example, a frequency synthesizer 112 can be configured to generate three waveforms having frequencies A, B, and C. Initially, the X-coil can be set to provide a portion of the magnetic field at frequency A, the Y-coil can be set to provide a portion of the magnetic field at frequency B, and the Z-coil can be set to provide a portion of the magnetic field at frequency C. The demodulating signal 116 is a mathematically created signal that generates the same frequencies A, B, and C as those generated by the frequency synthesizer 112 and the transmitter 110. The demodulating signal 116 is locked to the sensor signal. In particular, the x-coil, the y-coil, and the z-coil of the sensor 106 are each locked to frequency A, frequency B, and frequency C. Each frequency A, B, and C can be locked either in-phase or out-of-phase (e.g., 180 degrees off). A frequency that is locked out-of-phase can be represented with a negative sign.

At this point, if the orientation of the sensor 106 was known to be non-reversed at the time of locking, all frequencies A, B, and C could be determined to be locked in-phase and no further analysis would be required. For example, when the sensor 106 assumed a reversed orientation, the sensor signal would also reverse. However, the systems and techniques described herein do not require the sensor 106 to be maintained in a non-reversed orientation at the time of initialization; rather, the orientation of the sensor 106 is determined by rotating the frequencies at which the transmitter coils X-, Y-, and Z-run (e.g., while maintaining the locking of the demodulating signal 116 to the sensor signal) and observing the sign changes of the components of the sensor signal. A correlation can be determined between the signs of components of the sensor signal and the orientation of the sensor. If it is determined that any of the frequencies have been locked to the sensor signal out-of-phase, the system can mathematically correct the sensor signal to compensate for the components of the sensor signal that have an incorrect sign.

If the geometric orientation convention of the transmitter 110 is unknown (e.g., if it is unknown whether the transmitter 110 is right-handed or left-handed), there are eight possible combinations for the in-phase/out-of-phase status of each frequency A, B, and C:
1—All in-phase
2—All out-of-phase
3—only frequency A out-of-phase
4—only frequency B out-of-phase
5—only frequency C out-of-phase
6—only frequencies A and B out-of-phase
7—only frequencies B and C out-of-phase
8—only frequencies A and C out-of-phase.

However, if the geometric orientation convention of the transmitter 110 is known to be right-handed (e.g., the transmitter has a coordinate system that follows the right-hand rule), then the S-matrix should be a right-handed matrix. If the transmitter 110 is left-handed, then the S-matrix should be a left-handed matrix. In general, if the measured S-matrix has an orientation that does not match the handedness of the transmitter 110, the S-matrix can be forced into the opposite orientation (e.g., right-handed to left-handed or left-handed to right-handed) to match the handedness of the transmitter 110 by changing the signs of the components in one of the columns (e.g., the X column).

Once the S-matrix is known to be right-handed (e.g., if the transmitter 110 is right-handed) or known to be left-handed (e.g., if the transmitter 110 is left-handed), the total number of possible in-phase/out-of-phase combinations is reduced to four:
1—All in-phase
2—only frequencies A and B out-of-phase
3—only frequencies B and C out-of-phase
4—only frequencies A and C out-of-phase.

To determine which of the four possible combinations the currently locked frequencies fall into, the frequencies of the transmitter coils can be rotated. For example, the X-coil can provide a portion of the magnetic field at frequency B, the Y-coil can provide a portion of the magnetic field at frequency C, and the Z-coil can provide a portion of the magnetic field at frequency A. Throughout the rotation, the frequency synthesizer 112 maintains continuous generation of the waveforms A, B, and C, with no discontinuities in mathematical waveforms. In other words, mathematically continuous waveforms are each physically re-routed to the different transmitter coils. Likewise, the demodulation phases on the sensor signal (e.g., the PLL 114) are continuous and stable through and after frequency rotation.

Figure 3A:
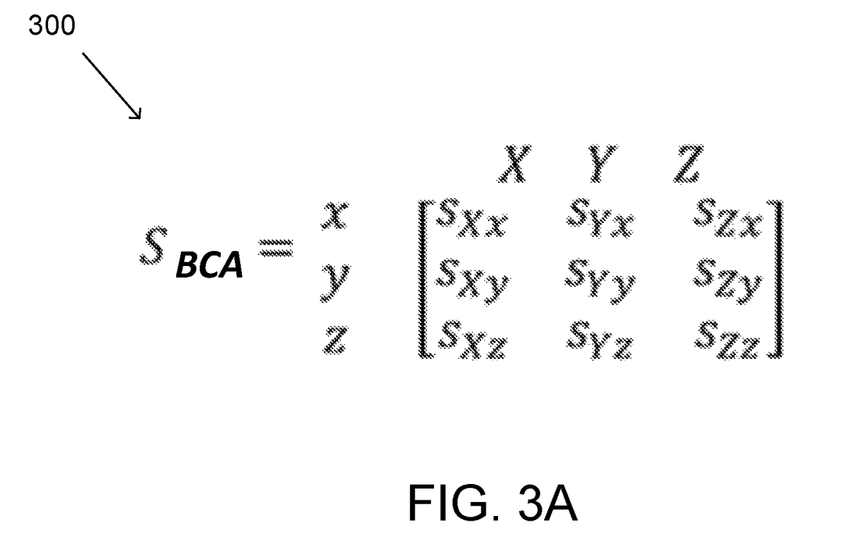
FIGS. 3A and 3B show examples of sensor signals in matrix representation after coils of the transmitter rotate the frequencies at which they run.

The sensor 106 then provides another sensor signal, which is denoted as sensor signal $S_{BCA}$. The first sensor signal $S_{ABC}$ and the second sensor signal $S_{BCA}$ are compared. Referring to FIG. 3A, which shows a matrix representation 300 of $S_{BCA}$, if all components of $S_{ABC}$ are equal to all components of $S_{BCA}$ (e.g., scenario 1), then it is confirmed that all frequencies A, B, and C are locked in-phase and no further adjustment or analysis is required. In other words, for future measurements by the sensor 106, the polarities of the sensor measurements are commensurate with the orientation of the sensor 106 such that the sensor signal polarities will reverse when the sensor 106 has a reversed orientation in the respective axis.

Figure 3B:
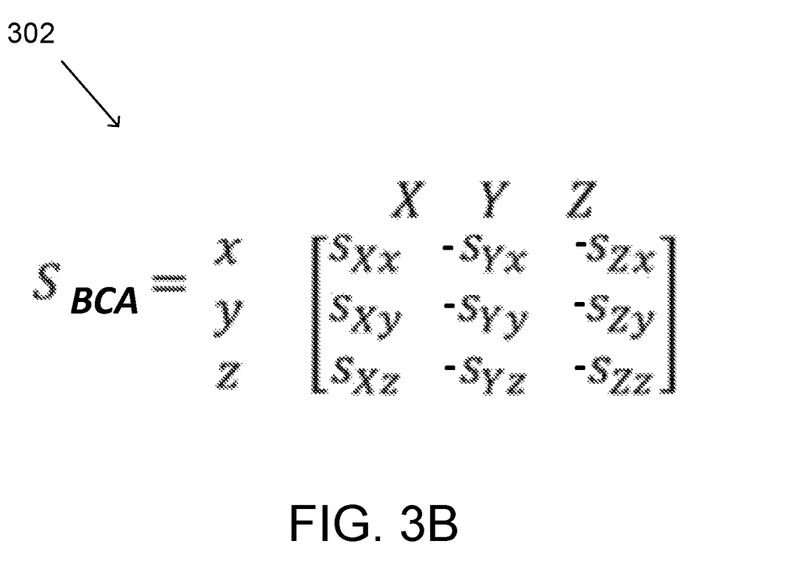

Alternatively, two of the frequencies may be locked out-of-phase. Referring to FIG. 3B, which shows another matrix representation 302 of $S_{BCA}$, if two of the frequencies are locked out-of-phase (e.g., scenario 2, 3, or 4), two of the columns of the S-matrix will change sign. In the illustrated example, the components in the Y-coil column and the components in the Z-coil column change sign, while the components in the X-coil column maintain their sign. The column that keeps its sign (e.g., in this case the X-coil column) points to the two channels that are locked out-of-phase. For example, the X-coil ran at frequency A for the first sensor signal $S_{ABC}$ and frequency B for the second sensor signal $S_{BCA}$, indicating that frequencies A and B have been locked out-of-phase (e.g., scenario 2).

Once it is determined which two frequencies are out-of-phase, future sensor signals can be mathematically compensated (e.g., by the computer 108) to correct for the out-of-phase frequencies. For example, with the X-coil running at frequency A, the Y-coil running at frequency B, and the Z-coil running at frequency C, because frequencies A and B were determined to be locked to the sensor signal out-of-phase, the signs of the components in the X and Y columns of the S-matrix will be the opposite of the true orientation of the sensor 106. In particular, when the sensor 106 is in a positive orientation in the x- and y-axes of the right-handed coordinate system, the sensor signal will incorrectly indicate negative orientation components. To correct for this, the computer 108 can be configured to reverse the signs of the components of the X and Y columns of the sensor signal such that the sensor signal provides a true indication of the orientation of the sensor 106. Such corrections occur outside of the PLL 114. In some implementations, alternatively, the computer 108 may be configured to change a phase of the demodulating signal 116 to force the channels to become locked in-phase, in which case the signs of the components of the X and Y columns of the sensor signal need not be reversed. For example, the phase of the demodulating signal 116 may be changed to force the frequencies that are locked out-of-phase to become locked in-phase. In other words, continuing with the example provided above, the sensor coils can be locked to frequency −A and −B (e.g., 180 degrees off).

In some implementations, a time-division-multiplexing technique may be used to excite the X-, Y-, and Z-coils of the transmitter 110 to generate the EM field. For example, each of the coils of the transmitter 110 may be configured to run at a single, same frequency (e.g., frequency A), and each of the coils may be excited one at a time (e.g., in series). During excitation of each of the transmitter coils, the coils of the sensor 106 (e.g., the x-, y-, and z-coils) can obtain measurements for the X-component, the Y-component, and the Z-component of the EM field, thereby resulting in a 3×3 S-matrix.

In some implementations (e.g., when a time-division-multiplexing technique is used), a demodulating signal for only a single frequency (e.g., frequency A) may be required. The demodulating signal is locked to the sensor signal. In particular, the x-coil, the y-coil, and the z-coil of the sensor 106 are each locked to frequency A. Similar to the example described above, the demodulating signal can be locked either in-phase or out-of-phase.

To determine whether the demodulating signal is locked in-phase or out-of-phase, the S-matrix can be analyzed to determine a geometric orientation convention in which the sensor signal is expressed. For example, a determination can be made as to whether the S-matrix is right-handed or left-handed. If the geometric orientation convention of the transmitter 110 does not match the geometric orientation convention of the S-matrix (e.g., if the transmitter 110 is right-handed yet the S-matrix is left-handed, or if the transmitter 110 is left-handed yet the S-matrix is right-handed), then the demodulating signal is determined to be locked to the sensor signal out-of-phase (e.g., the sensor coils are determined to be locked to frequency A out-of-phase).

If the demodulating signal is determined to be locked to the sensor signal out-of-phase, the system can make one or more corrections to compensate for such. For example, the signs of the components of the sensor signal can be reversed. Such corrections occur outside of the PLL. In some implementations, alternatively, a phase of the demodulating signal may be changed to force frequency A to be locked in-phase, in which case the signs of the components of the sensor signal need not be reversed. For example, the sensor coils can be locked to frequency −A (e.g., 180 degrees off).

The EMT system described above can be implemented using software included on a computer-readable medium for execution on a computer (e.g., the computer 108 of FIG. 1). For example, the software may form procedures in one or more computer programs that execute on one or more programmed or programmable computer systems (which may be of various architectures) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer may be stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The system may also be considered to be implemented as a computer-readable storage medium, configured with a computer program, where the storage medium so configured causes a computer system to operate in a specific and predefined manner to perform the functions described herein.

A number of embodiments have been described. Nevertheless, it will be understood that various modifications may be made without departing from the spirit and scope of the subject matter described herein. Other such embodiments are within the scope of the following claims.

What is claimed is:

1. A system comprising:
a transmitter that includes at least three coils, the transmitter configured to generate magnetic fields;
a sensor that includes at least three coils, the sensor configured to provide sensor signals that correspond to the magnetic fields generated by the transmitter; and
a computing device in communication with the transmitter and the sensor, the computing device configured to:
cause the transmitter to generate a first magnetic field in which a first transmitter coil provides a portion of the first magnetic field at a first frequency, a second transmitter coil provides a portion of the first magnetic field at a second frequency, and a third transmitter coil provides a portion of the first magnetic field at a third frequency, wherein the first frequency, the second frequency, and the third frequency are generated by a frequency synthesizer that provides at least one waveform to the transmitter for generating the first magnetic field;
receive, from the sensor, a first sensor signal that corresponds to the first magnetic field, wherein the first sensor signal includes, for each sensor coil, a measurement component that corresponds to each transmitter coil, wherein the first sensor signal is locked to a demodulating signal using a phase-locked loop such that a first sensor coil, a second sensor coil, and a third sensor coil are each locked to the first frequency, the second frequency, and the third frequency;
cause the transmitter to generate a second magnetic field in which the first transmitter coil provides a portion of the second magnetic field at the second frequency, the second transmitter coil provides a portion of the second magnetic field at the third frequency, and the third transmitter coil provides a portion of the second magnetic field at the first frequency;
receive, from the sensor, a second sensor signal that corresponds to the second magnetic field, wherein the second sensor signal includes, for each sensor coil, a measurement component that corresponds to each transmitter coil;
compare the first sensor signal and the second sensor signal; and
based on the comparison, determine whether any of the sensor coils are locked to its corresponding frequency out-of-phase.

2. The system of claim 1, wherein comparing the first sensor signal and the second sensor signal comprises:
comparing the signs of the measurement components that correspond to the first transmitter coil in the first sensor signal to the signs of the measurements components that correspond to the first transmitter coil in the second sensor signal;
comparing the signs of the measurement components that correspond to the second transmitter coil in the first sensor signal to the signs of the measurements components that correspond to the second transmitter coil in the second sensor signal; and
comparing the signs of the measurement components that correspond to the third transmitter coil in the first sensor signal to the signs of the measurements components that correspond to the third transmitter coil in the second sensor signal.

3. The system of claim 2, wherein:
if the signs of the measurement components that correspond to the first transmitter coil in the first sensor signal are the same as the signs of the measurements components that correspond to the first transmitter coil in the second sensor signal, a determination is made that the first frequency and the second frequency are locked out-of-phase;
if the signs of the measurement components that correspond to the second transmitter coil in the first sensor signal are the same as the signs of the measurements components that correspond to the second transmitter coil in the second sensor signal, a determination is made that the second frequency and the third frequency are locked out-of-phase; and
if the signs of the measurement components that correspond to the third transmitter coil in the first sensor signal are the same as the signs of the measurements components that correspond to the third transmitter coil in the second sensor signal, a determination is made that the third frequency and the first frequency are locked out-of-phase.

4. The system of claim 3, wherein the computing device is further configured to mathematically correct sensor signals provided by the sensor based on the determination of whether any of the sensor coils are locked to its corresponding frequency out-of-phase.

5. The system of claim 4, wherein mathematically correcting the sensor signals comprises changing a sign of measurement components of the sensor signals.

6. The system of claim 5, wherein the first sensor signal and the second sensor signal are locked to the demodulating signal by a phase-locked loop, and mathematically correcting the sensor signals provided by the sensor occurs outside of the phase-locked loop.

7. The system of claim 3, wherein the computing device is further configured to change a phase of the demodulating signal to cause the frequencies that are determined to be locked out-of-phase to become locked in-phase.

8. The system of claim 1, wherein the first sensor signal and the second sensor signal comprise voltages that are generated based on interaction between the sensor and the magnetic field generated by the transmitter.

9. The system of claim 8, wherein values of the voltages are indicative of the orientation and position of the sensor relative to the transmitter.

10. The system of claim 1, wherein the sensor is a three-axis sensor that includes a concentric, collocated set of sensor coils.

11. The system of claim 1, wherein the transmitter is a three-axis transmitter that includes a concentric, collocated set of transmitter coils.

12. The system of claim 1, wherein the first sensor signal and the second sensor signal are locked to the demodulating signal by a phase-locked loop.

13. The system of claim 1, wherein the frequency synthesizer is configured to continuously generate a first waveform of the first frequency, a second waveform of the second frequency, and a third waveform of the third frequency.

14. The system of claim 13, wherein the first waveform is provided to the first transmitter coil during generation of the first magnetic field, the second waveform is provided to the second transmitter coil during generation of the first magnetic field, and the third waveform is provided to the third transmitter coil during generation of the first magnetic field.

15. The system of claim 13, wherein the first waveform is provided to the third transmitter coil during generation of the second magnetic field, the second waveform is provided to the first transmitter coil during generation of the second magnetic field, and the third waveform is provided to the second transmitter coil during generation of the second magnetic field.

16. The system of claim 13, wherein the first waveform is re-routed from the first transmitter coil to the third transmitter coil, the second waveform is re-rerouted from the second transmitter coil to the first transmitter coil, and the third waveform is re-routed from the third transmitter coil to the second transmitter coil, when the transmitter begins to generate the second magnetic field.

17. The system of claim 16, wherein the first waveform, the second waveform, and the third waveform are each physically re-routed.

18. The system of claim 16, wherein the second sensor signal is locked to the demodulating signal by the phase-locked loop, and demodulation phases of the phase-locked loop are continuous and stable throughout and after the re-routing of the waveforms.

19. A method comprising:
causing a transmitter to generate a first magnetic field in which a first transmitter coil provides a portion of the first magnetic field at a first frequency, a second transmitter coil provides a portion of the first magnetic field at a second frequency, and a third transmitter coil provides a portion of the first magnetic field at a third frequency, wherein the first frequency, the second frequency, and the third frequency are generated by a frequency synthesizer that provides at least one waveform to the transmitter for generating the first magnetic field;
receiving, from a sensor, a first sensor signal that corresponds to the first magnetic field, wherein the first sensor signal includes, for each of at least three sensor coils, a measurement component that corresponds to each transmitter coil, wherein the first sensor signal is locked to a demodulating signal using a phase-locked loop such that a first sensor coil, a second sensor coil, and a third sensor coil are each locked to the first frequency, the second frequency, and the third frequency;
causing the transmitter to generate a second magnetic field in which the first transmitter coil provides a portion of the second magnetic field at the second frequency, the second transmitter coil provides a portion of the second magnetic field at the third frequency, and the third transmitter coil provides a portion of the second magnetic field at the first frequency;
receiving, from the sensor, a second sensor signal that corresponds to the second magnetic field, wherein the second sensor signal includes, for each sensor coil, a measurement component that corresponds to each transmitter coil;
comparing the first sensor signal and the second sensor signal; and
based on the comparison, determining whether any of the sensor coils are locked to its corresponding frequency out-of-phase.

20. A computer-readable medium comprising instructions that when executed by a processor perform a method comprising:

causing a transmitter to generate a first magnetic field in which a first transmitter coil provides a portion of the first magnetic field at a first frequency, a second transmitter coil provides a portion of the first magnetic field at a second frequency, and a third transmitter coil provides a portion of the first magnetic field at a third frequency, wherein the first frequency, the second frequency, and the third frequency are generated by a frequency synthesizer that provides at least one waveform to the transmitter for generating the first magnetic field;

receiving, from a sensor, a first sensor signal that corresponds to the first magnetic field, wherein the first sensor signal includes, for each of at least three sensor coils, a measurement component that corresponds to each transmitter coil, wherein the first sensor signal is locked to a demodulating signal using a phase-locked loop such that a first sensor coil, a second sensor coil, and a third sensor coil are each locked to the first frequency, the second frequency, and the third frequency;

causing the transmitter to generate a second magnetic field in which the first transmitter coil provides a portion of the second magnetic field at the second frequency, the second transmitter coil provides a portion of the second magnetic field at the third frequency, and the third transmitter coil provides a portion of the second magnetic field at the first frequency;

receiving, from the sensor, a second sensor signal that corresponds to the second magnetic field, wherein the second sensor signal includes, for each sensor coil, a measurement component that corresponds to each transmitter coil;

comparing the first sensor signal and the second sensor signal; and based on the comparison, determining whether any of the sensor coils are locked to its corresponding frequency out-of-phase.

21. A system comprising:

a transmitter that includes at least three coils, the transmitter configured to generate magnetic fields;

a sensor that includes at least three coils, the sensor configured to provide sensor signals that correspond to the magnetic fields generated by the transmitter; and a computing device in communication with the transmitter and the sensor, the computing device configured to:
cause the transmitter to generate a magnetic field according to a time-division-multiplexing technique in which a first transmitter coil provides a portion of the magnetic field at a particular frequency, a second transmitter coil provides a portion of the magnetic field at the particular frequency, and a third transmitter coil provides a portion of the magnetic field at the particular frequency, wherein the particular frequency is generated by a frequency synthesizer that provides at least one waveform to the transmitter for generating the magnetic field, and wherein the transmitter coils are exited one at a time such that the respective portions of the magnetic field are provided one at a time;

receive, from the sensor, a sensor signal that corresponds to the magnetic field, wherein the sensor signal includes, for each sensor coil, a measurement component that corresponds to each transmitter coil, wherein the sensor signal is locked to a demodulating signal using a phase-locked loop such that a first sensor coil, a second sensor coil, and a third sensor coil are each locked to the particular frequency;

determine whether the sensor signal is expressed in a geometric orientation convention that matches a geometric orientation convention of the transmitter; and if the geometric orientation convention of the sensor signal is determined to not match the geometric orientation convention of the transmitter, determine that the demodulating signal is locked to the sensor signal out-of-phase.

22. The system of claim 21, wherein determining that the demodulating signal is locked to the sensor signal out-of-phase comprises determining that the sensor coils are locked to the particular frequency out-of-phase.

23. The system of claim 21, wherein the computing device is further configured to change a phase of the demodulating signal to cause the particular frequency to become locked in-phase.

24. The system of claim 21, wherein the geometric orientation convention of the sensor signal and the geometric orientation convention of the transmitter are each either right-handed or left-handed.

25. The system of claim 24, wherein the transmitter is right-handed if the transmitter has a coordinate system that follows the right-hand rule, and the transmitter is left-handed if the transmitter has a coordinate system that follows the left-hand rule.

* * * * *